United States Patent [19]

Matthews

[11] Patent Number: 4,632,112
[45] Date of Patent: Dec. 30, 1986

[54] PROCEDURE FOR DRAINING FLUID FROM LUNGS

[76] Inventor: Hugoe R. Matthews, The Department of Thoracic Surgery, East Birmingham Hospital, Bordesley Green East, Birmingham B9 5ST, England

[21] Appl. No.: 525,923

[22] Filed: Aug. 24, 1983

[30] Foreign Application Priority Data

Oct. 27, 1982 [GB] United Kingdom ................ 8230714

[51] Int. Cl.⁴ ............................................ A61F 17/32
[52] U.S. Cl. .................................................. 128/305.3
[58] Field of Search ...................... 128/200.26, 207.14, 128/329, 330, 305.3

[56] References Cited

U.S. PATENT DOCUMENTS

| | | | |
|---|---|---|---|
| 2,865,374 | 12/1958 | Brown et al. | 128/305.3 |
| 2,873,742 | 2/1959 | Shelden | 128/305.3 |
| 3,643,649 | 2/1972 | Amato | 128/305.3 |
| 4,444,185 | 4/1984 | Shugar | 128/305.3 |

FOREIGN PATENT DOCUMENTS 1384682 11/1964 France ................................ 128/305.3

*Primary Examiner*—Gene Mancene
*Assistant Examiner*—Wenceslao J. Contreras
*Attorney, Agent, or Firm*—Pollock, Vande Sande & Priddy

[57] ABSTRACT

Removal of fluid from a patient's lungs is achieved using a small diameter outer guide tube, the machine end of which is bifurcated into two wings. A small cut is first made into the trachea and a stylet is pushed through the cut. The guide tube is then inserted into the trachea by sliding along the stylet until the machine end of the tube protrudes from the patient's neck. After removal of the stylet the wings of the tube are sutured to the patient's skin. A suction catheter having a set curvature can then be introduced to either of the patient's lungs, via the guide tube, to remove fluid. The diameter of the guide tube is less than that of the trachea so that air passage along the trachea is not impeded.

7 Claims, 10 Drawing Figures

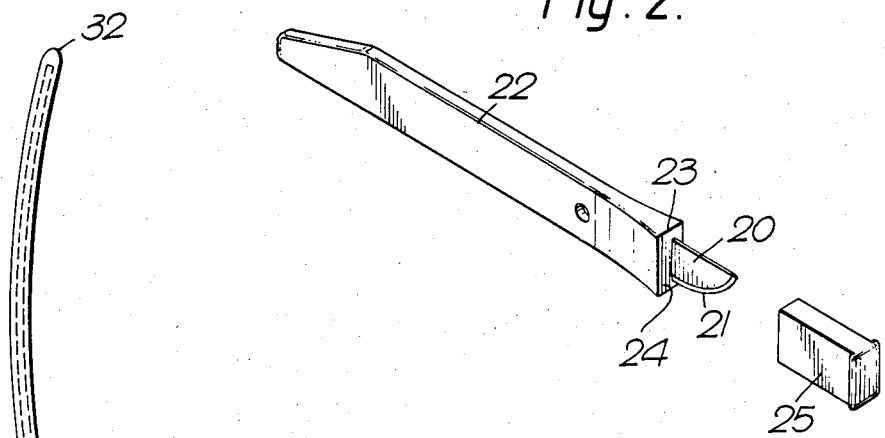
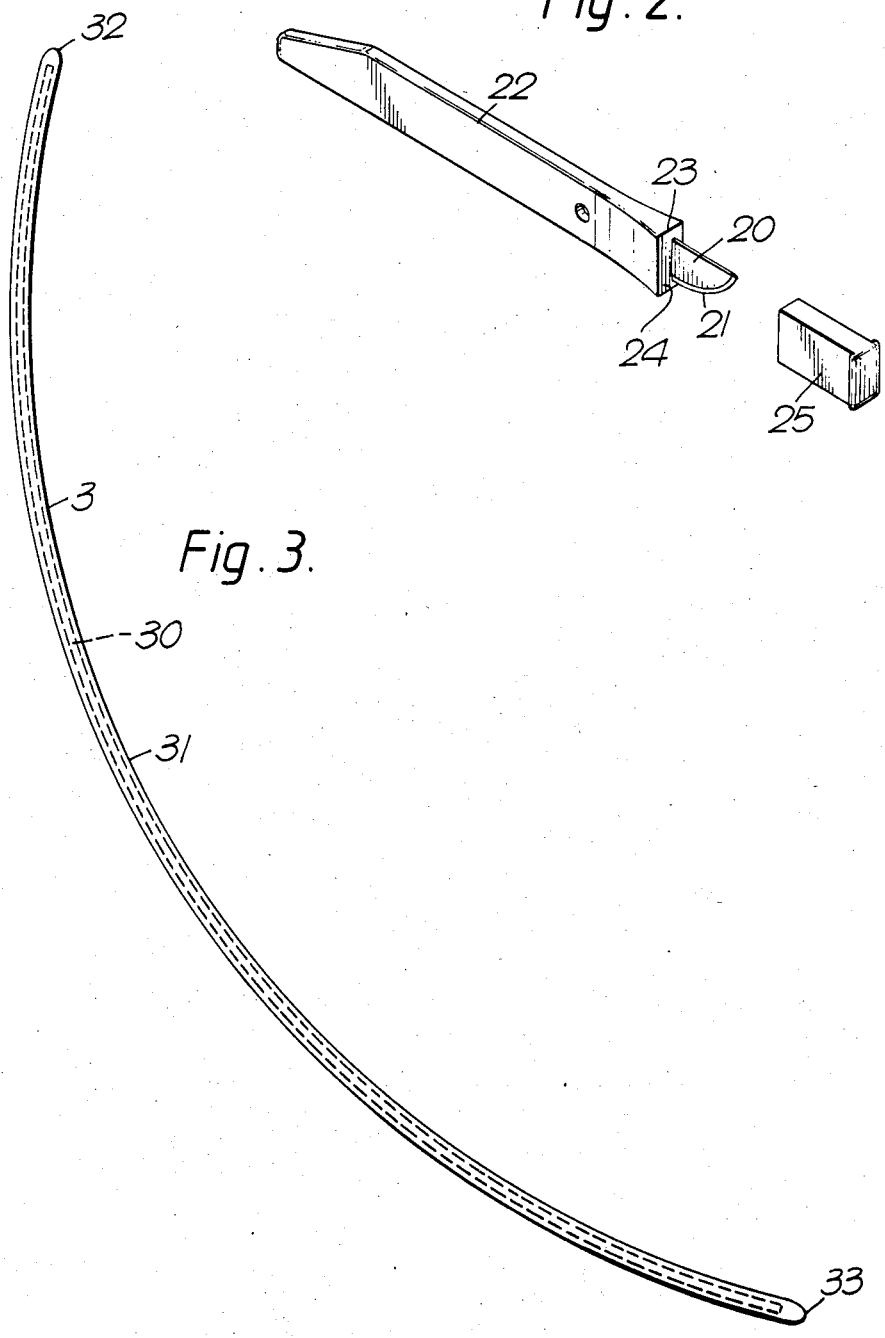

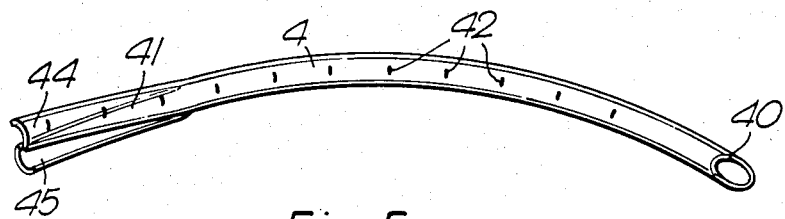
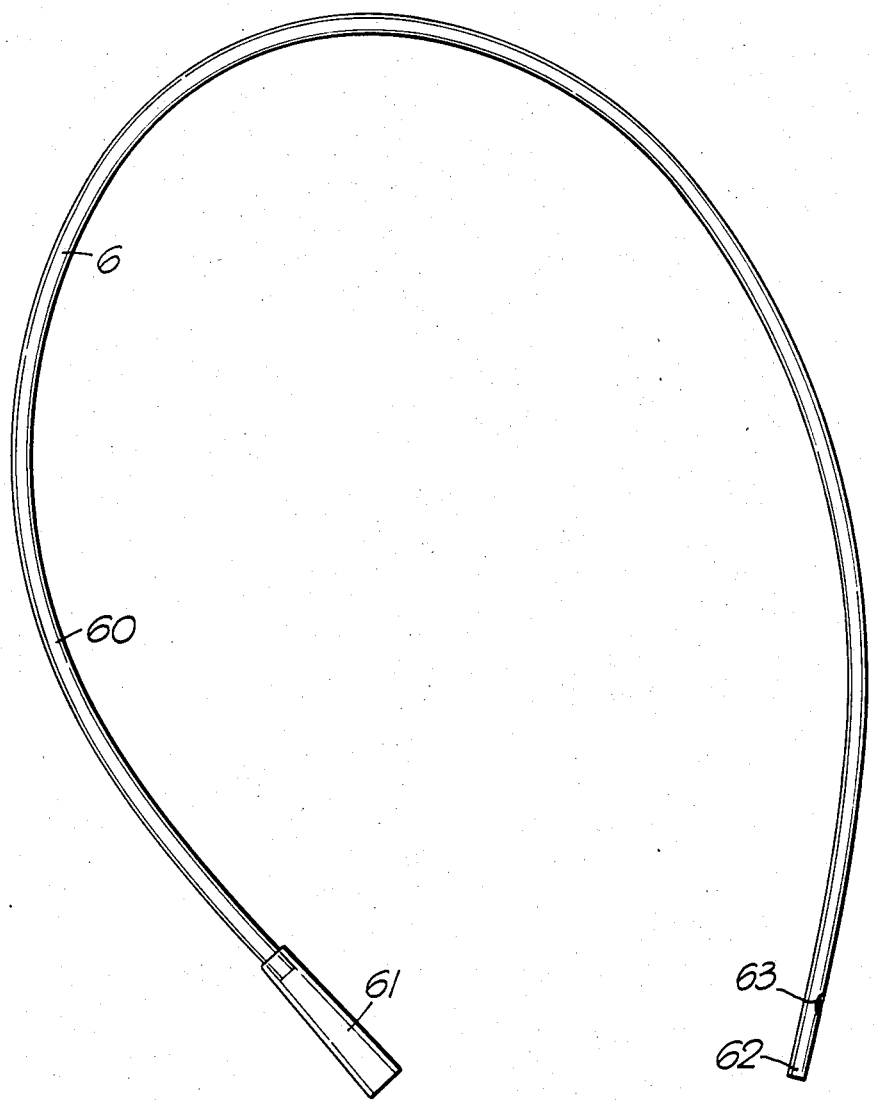

PROCEDURE FOR DRAINING FLUID FROM LUNGS

BACKGROUND OF THE INVENTION

This invention relates to medical apparatus and procedures.

The invention is more particularly concerned with the removal of fluid from patients' lungs.

Retention of sputum is a major cause of morbidity and mortality following thoracic surgery. The usual treatment of such conditions is by tracheostomy, that is, by making a stoma or opening through the wall of the patient's trachea and introducing a tracheostomy tube which is sealed about its outer surface with the inner surface of the trachea. The patient breathes through the tracheostomy tube which is also used as a guide for the periodic introduction of a suction catheter by which sputum can be removed from the patient's lungs.

This treatment has several disadvantages. Because the tracheostomy tube is of large diameter or is sealed with the trachea, thereby preventing airflow to the patient's mouth, he is unable to cough and clear sputum naturally. The introduction and use of the tracheostomy tube commonly causes distress and discomfort to the patient. Damage can be caused to the interior of the trachea by the use of such tubes and the opening in the wall of the trachea can take a long time to heal fully after removal of the tube.

BRIEF SUMMARY OF THE INVENTION

It is an object of the present invention to provide apparatus and a procedure whereby the above-mentioned disadvantages can be alleviated.

According to one aspect of the present invention there is provided a method of removing fluid from the lungs of a patient comprising the steps of: making a small cut through the patient's throat into the trachea; introducing an outer guide tube through said cut so that a part of it extends into the trachea, the diameter of said guide tube being substantially less than the internal diameter of said trachea such that air flow through said trachea around said guide tube is substantially unimpeded; introducing a suction catheter to the patient's lungs through said guide tube; and applying suction to the suction catheter so as to remove fluid in the lungs.

A stylet may be introduced through said cut prior to said guide tube, said guide tube being slid into the trachea along said stylet, and said stylet being withdrawn to leave said guide tube in situ prior to insertion of said suction catheter. The machine end of said guide tube may be bifurcated, the guide tube being secured to the patient by bending the bifurcated parts of the tube and securing them to the patient's skin. The patient end of said guide tube may have an angled end. The suction catheter may be curved along its length so as to enable it to be directed into one or other of the patient's lungs.

Because the trachea is not blocked by the outer guide tube, the patient is able to breathe and cough normally, thereby itself helping to reduce sputum and reduce morbidity and mortality. The cut necessary for the introduction of the outer guide tube can be small, since, typically the guide tube is only 5.4 mm in outer diameter; this ensures that the wound heals quickly.

According to another aspect of the present invention, there is provided apparatus for use in the removal of fluid from the lungs of a patient comprising: an outer guide tube that is adapted for insertion into the trachea of the patient through a cut in the patient's throat, so that one end of the guide tube is located within the trachea and the other end is located outside the trachea for reception of the end of a suction catheter that can be inserted through said guide tube beyond said one end for removal of said fluid, wherein said guide tube is of a size such that normal air flow along the patient's trachea is substantially unimpeded.

The said other end of the guide tube may be bifurcated such that the guide tube can be secured to the patient by bending the bifurcated parts of the tube and securing them to the patient's skin. The outer diameter of said guide tube may be about 5 mm.

According to a further aspect of the present invention there is provided a kit for use in the removal of fluid from the lungs of a patient comprising: an outer guide tube that is adapted for insertion into the trachea of a patient through a cut in the patient's throat, so that one end of the guide tube is located within the trachea and the other end is located outside the trachea, the said guide tube being of a size such that normal air flow along the patient's trachea is substantially unimpeded; and a suction catheter that is adapted for insertion into the patient's lungs through said guide tube.

The kit may further include a stylet along which said guide tube can be slid into the trachea, and a knife for use in making said cut, said knife being provided with stop means to limit the extent of penetration and to prevent damage to the posterior of the trachea.

A kit including apparatus for removing fluid from a patient's lungs, and a procedure for using this apparatus, in accordance with the present invention, will now be described, by way of example, with reference to the accompanying drawings.

BRIEF DESCRIPTION OF THE DRAWINGS

FIGS. 2 to 5 show components of the kit in more detail; and

DETAILED DESCRIPTION

Figure 1:
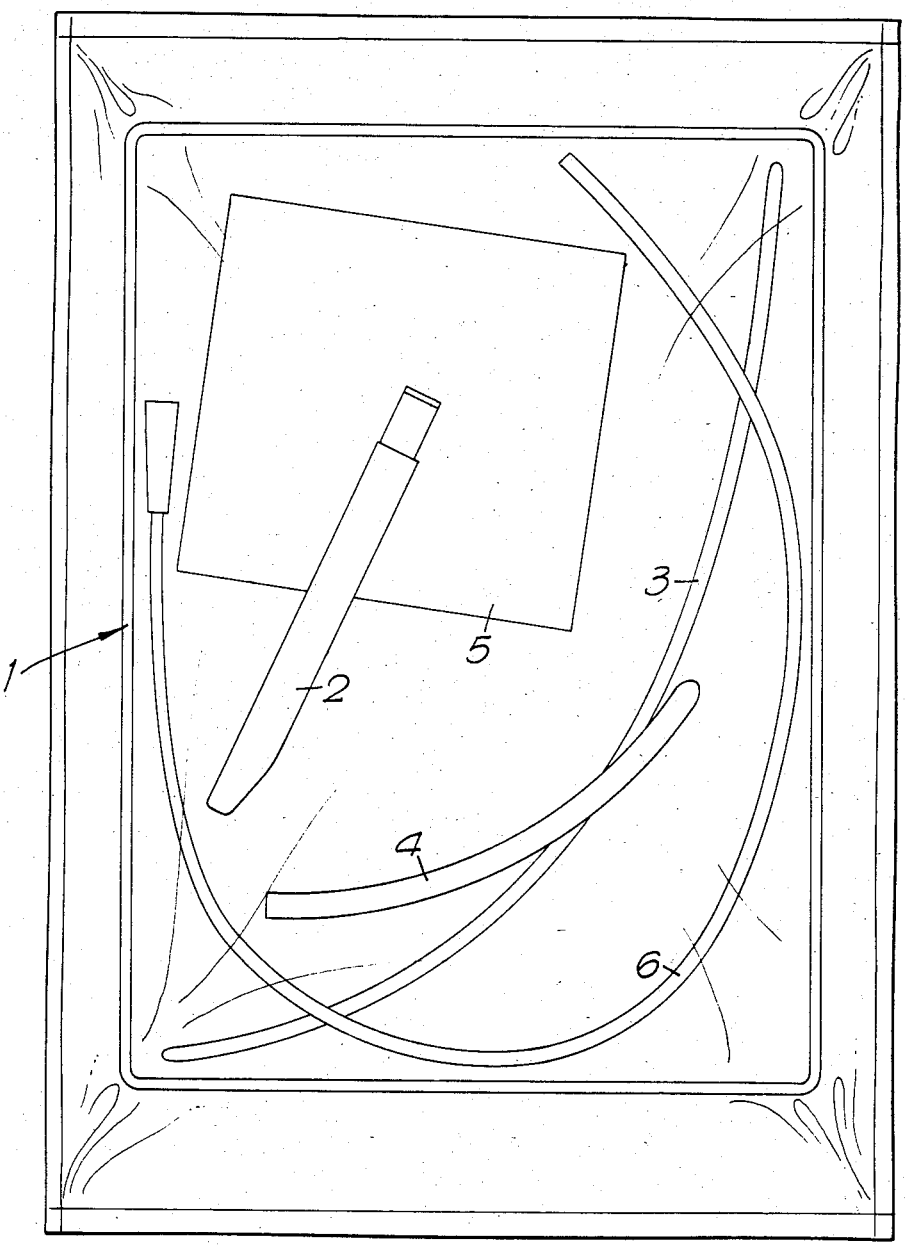
FIG. 1 shows the kit schematically.

With reference to FIG. 1, the apparatus is packed as a kit 1 comprising a scalpel 2, a stylet 3, an outer guide tube 4, a suture and needle pack 5 and a suction catheter 6.

The scalpel 2, as shown in FIG. 2, has a metal blade 20 with an arcuate cutting edge 21, the blade being moulded in a plastics handle 22. The forward end 23 of the handle 22 provides flat shoulders or stops 24 on either side of the blade 20 which limit the extent of its penetration. The blade 20 is 14 mm long so that it can cut through the anterior wall of the trachea but is prevented from cutting the posterior wall by engagement of the shoulders 24 with the outer surface of the patient's throat. The blade 20 is protected, in the kit 1, by a push-on cover 25.

With reference now to FIG. 3, the stylet 3 is 280 mm long and is curved in an arc of radius about 180 mm. The outer diameter of the stylet 3 is about 3.5 mm and is formed by a metal rod 30 extending within a sealed sleeve 31 of plastics material. The ends 32 and 33 of the stylet 3 are rounded to prevent damage and aid insertion. The metal rod 30 makes the stylet 3 rigid and gives it a degree of resilience.

The outer guide tube 4, shown in more detail in FIG. 4, is in the form of a curved plastics tube 130 mm long that is open at both ends 40 and 41. The tube 4 has an outer diameter of 5.4 mm and an inner diameter of 4 mm, its curvature being substantially the same as that of the stylet 3. Although in its natural state the guide tube 4 is curved, it is of a relatively soft, flexible plastics material which enables it to be straightened or bent as desired. At its patient end 40, the tube 4 is cut at an angle of about 45° to the plane in which the tube lies. The tube 4 bears markings 42 at 10 mm intervals along its length, from its patient end 40, so that the location of the patient end can be readily determined. At its machine end 41 the tube 4 is cut off square. The tube 4 also has a 30 mm longitudinal cut on a diameter at its machine end so that it is bifurcated and can be separated into two wings 44 and 45.

The suction catheter 6, shown in FIG. 5, is of conventional form, being provided by a transparent plastics tube 60 that is 420 mm long, and that has an outer diameter of 3.5 mm. At its machine end, the tube 60 is joined with a female luer connector 61. At its patient end 62 the tip of the tube is rounded and has a small eliptical side port 63 formed in its wall 10 mm from the end of the tube.

Figure 6:
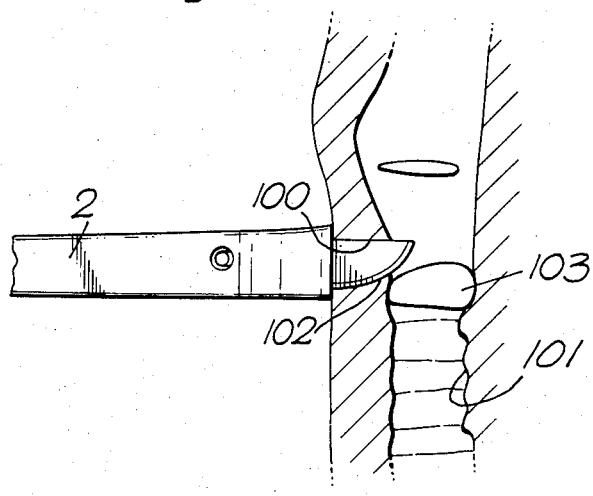
FIGS. 6 to 10 show various steps in the procedure.
Figure 7:
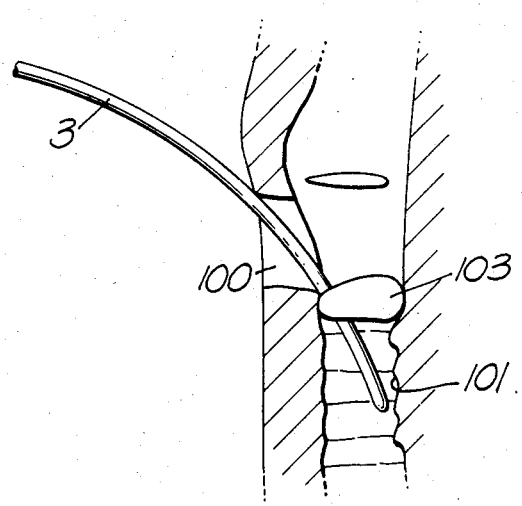
Figure 8:
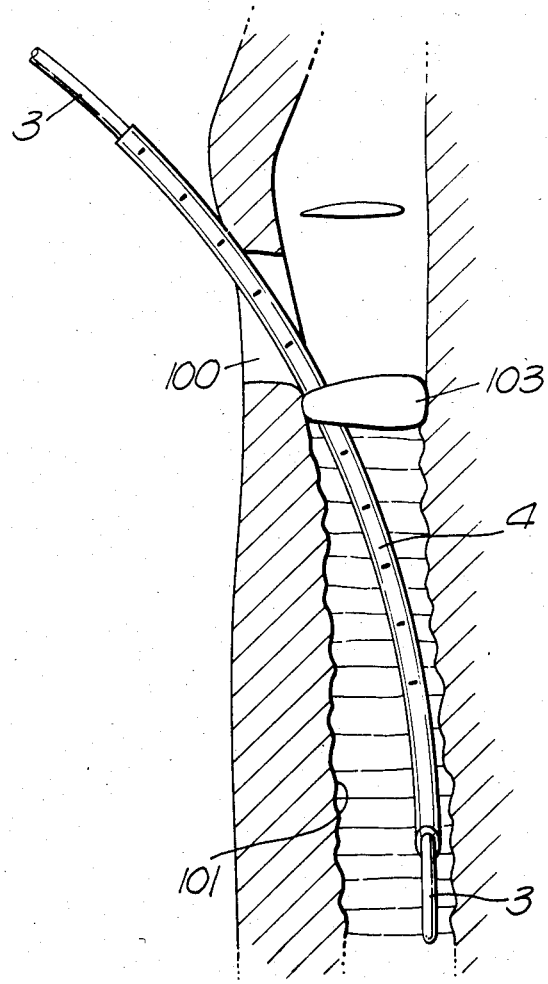

The apparatus is used in the manner shown in FIGS. 6 to 10. First, as shown in FIG. 6, a small cut 100 is made into the trachea 101 with the scalpel 2 through the cricothyroid membrane 102 which lies above the cricoid cartilage 103; this cut can be simply a vertical slit 10 mm long. The stylet 3 is then pushed into the trachea 101 through the cut 100 so that about half its length is within the patient's body—as shown in FIG. 7. The next step is to slide the outer guide tube 4 along the stylet 3, as shown in FIG. 8, using the stylet to direct the guide tube 4 down the trachea until only 30 mm at the machine end of the tube projects from the cut.

Figure 9:
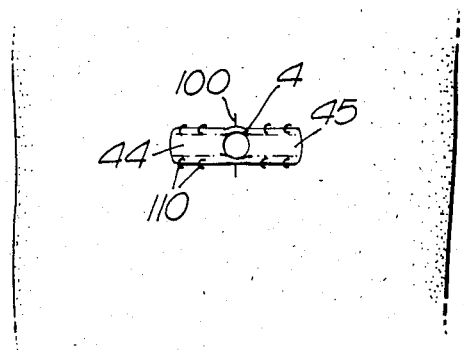
Figure 10:
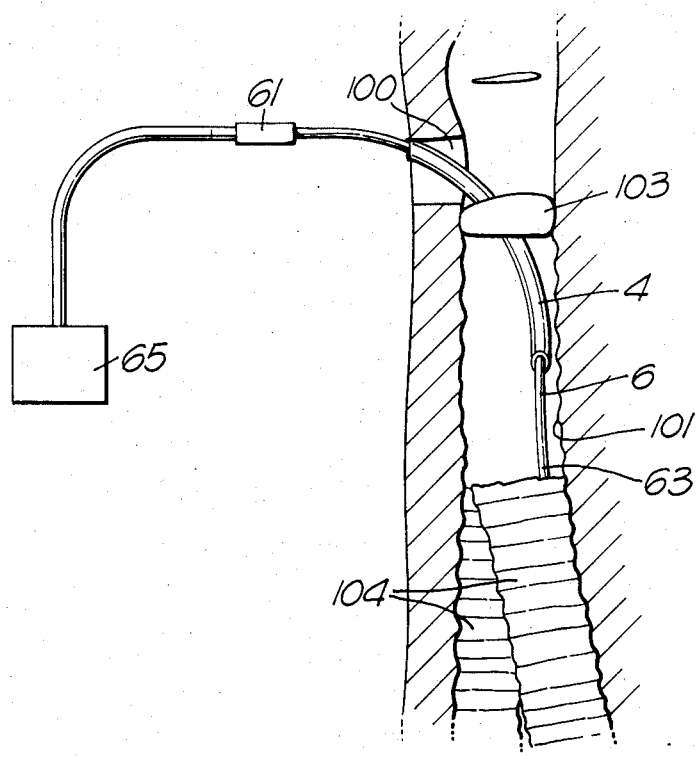

The stylet 3 is then removed and the wings 44 and 45 of the tube 4 are bent laterally and secured to the patient's neck by stitching a suture 110 through the wings and the patient's skin, in the manner shown in FIG. 9.

Since the guide tube 4 is substantially smaller than the normal adult trachea, and since it is not sealed with the inside of the trachea by an inflatable cuff or any other means, air flow along the trachea around the guide tube is substantially unimpeded and the patient is enabled to breathe and cough normally. The guide tube 4 can remain in position for several weeks.

Fluid in the patient's lungs can be removed periodically by mechanical means, making use of the guide tube 4. To do this, the patient end 63 of the suction catheter 6 is pushed through the guide tube 4, down the trachea 101 and into one or other of the patient's bronchi 104 in the manner shown in FIG. 10. The machine end connector 61 of the catheter 6 is then coupled to a suction pump 65 and suction is applied to withdraw fluid from the bronchi 104 and lungs. When no more fluid is being sucked up the catheter 6, it is removed, leaving the outer guide tube 4 in situ. This procedure is repeated periodically, such as every fifteen minutes, or whenever necessary. Even during the suction procedure the patient is caused little distress or discomfort since his breathing is substantially unimpaired. The suction catheter 6 would normally be bent in its packaging, thereby giving it a natural tendency to curve in one direction, this can be used to guide the end of the catheter down the desired bronchus and, after removal and reorientation, down the other bronchus, thereby ensuring that the maximum amount of fluid is removed from the lungs.

What I claim Is:

1. Apparatus for use in conducting a surgical procedure to remove fluid from a patient's lungs comprising in combination:
   a scalpel for making a small cut through the patient's throat into the trachea, said scalpel being provided with stop means to limit the extent of its penetration to thereby prevent damage to the posterior of the trachea,
   a stylet having a blunt, patient-end adapted for insertion into the trachea through the cut in a patient's throat;
   an outer, flexible guide tube adapted for insertion into the trachea on said stylet so that one end of the guide tube is located within the trachea and the other end is located outside the trachea, the external diameter of the guide tube being substantially less than the internal diameter of the human trachea such that airflow through said trachea around said guide tube is substantially unimpeded, and the internal diameter of the guide tube being substantially the same as the external diameter of the stylet; and
   a suction catheter adapted for insertion into the patient's lungs through said guide tube after removal of the stylet, the external diameter of said suction catheter being substantially the same as the internal diameter of the guide tube.

2. A method of removing fluid from the lungs of a patient comprising the steps of:
   using a scalpel provided with stop means to limit the extent of its trachea, making a small incision with a scalpel through the patient's throat into the trachea with the depth of the incision not exceeding that permitted by the stop means;
   introducing a blunt, patient-end of a stylet into the trachea through said incision;
   introducing a flexible outer guide tube extending around said stylet through the cut so that part of the outer guide tube extends into the trachea, the external diameter of said guide tube being substantially less than the internal diameter of said trachea such that air flow through said trachea around said guide tube is substantially unimpeded, the internal diameter of the guide tube being substantially the same as the external diameter of the stylet;
   removing said stylet so as to leave the outer guide tube in position;
   subsequently introducing a suction catheter to the patient's lungs through said guide tube, said suction catheter having an external diameter substantially the same as the internal diameter of the guide tube; and
   applying suction to the suction catheter to remove fluid from the lungs.

3. A method according to claim 2, wherein the machine end of said guide tube is bifurcated, and wherein the guide tube is secured to the patient by bending the bifurcated parts of the tube and securing them to the patient's skin.

4. A method according to claim 2, wherein the patient end of said guide tube has an angled end.

5. A method according to claim 2, wherein said suction catheter is curved along its length so as to enable it to be directed into one or other of the patient's lungs.

6. A method according to claim 2, wherein said stylet is curved along its length.

7. A method according to claim 2, wherein the outer diameter of said guide tube is about 5 mm.

* * * * *